(12) United States Patent
Heimel

(10) Patent No.: US 9,839,758 B2
(45) Date of Patent: Dec. 12, 2017

(54) WATER AND AIR PRECONDITIONING APPARATUS

(71) Applicant: Gregory Heimel, Saint Paul, MN (US)

(72) Inventor: Gregory Heimel, Saint Paul, MN (US)

(*) Notice: Subject to any disclaimer, the term of this patent is extended or adjusted under 35 U.S.C. 154(b) by 508 days.

(21) Appl. No.: 13/905,287

(22) Filed: May 30, 2013

(65) Prior Publication Data

US 2014/0158128 A1    Jun. 12, 2014

Related U.S. Application Data

(60) Provisional application No. 61/654,382, filed on Jun. 1, 2012.

(51) Int. Cl.
| | | |
|---|---|---|
| *A61M 16/10* | (2006.01) | |
| *A61L 2/10* | (2006.01) | |
| *A61L 9/20* | (2006.01) | |
| *A61M 16/06* | (2006.01) | |
| *A61M 16/12* | (2006.01) | |
| *A61M 16/16* | (2006.01) | |

(Continued)

(52) U.S. Cl.
CPC .......... *A61M 16/16* (2013.01); *A61M 16/105* (2013.01); *A61M 16/109* (2014.02); *A61M 16/0066* (2013.01); *A61M 16/06* (2013.01); *A61M 16/12* (2013.01); *A61M 16/14* (2013.01); *A61M 2205/053* (2013.01)

(58) Field of Classification Search
USPC ........................................................ 128/913
See application file for complete search history.

(56) References Cited

U.S. PATENT DOCUMENTS

| 1,893,670 A | * | 1/1933 | Goodner | ............... A61M 16/00 |
| | | | | 128/204.27 |
| 2,737,176 A | * | 3/1956 | Fox | ...................... A61M 16/00 |
| | | | | 128/204.25 |

(Continued)

OTHER PUBLICATIONS

"Got the CPAP Blues?—Five Common CPAP Issues and Five Easy Solutions," accessed on the Internet, Mar. 10, 2014. http://www.easybreathe.com/blog/got-cpap-blues-five-common-cpap-issues-five-easy-solutions/ (6 pages).

(Continued)

*Primary Examiner* — (Jackie) Tan-Uyen T Ho
*Assistant Examiner* — Joseph D Boecker
(74) *Attorney, Agent, or Firm* — Mitchell Hamline IP Clinic

(57) ABSTRACT

A fluid preconditioning apparatus used to pretreat fluids for an air disbursement machine. A first portion includes a first outlet for a treated gas, a second outlet for a treated liquid, a third outlet for a hose and a cover. A second portion includes a first inlet to receive a gas, a second inlet to receive liquid, a gas treatment chamber, a gas flow generator for moving the gas from the first inlet through the gas treatment chamber and the first outlet. The second portion also includes a liquid treatment chamber that connects to the second inlet, and a liquid flow generator for moving the liquid from the second inlet through the liquid treatment chamber and the second outlet. The gas treatment chamber treats gas by filtering and disinfecting the gas and the liquid treatment chamber creates the treated liquid by filtering and disinfecting the liquid.

20 Claims, 14 Drawing Sheets

(51) Int. Cl.
*A61M 16/00* (2006.01)
*A61M 16/14* (2006.01)

(56) References Cited

U.S. PATENT DOCUMENTS

| | | | | |
|---|---|---|---|---|
| 2,868,198 | A * | 1/1959 | Brooke | A61M 16/104 128/205.24 |
| 4,108,172 | A * | 8/1978 | Moore, Jr. | A62B 19/00 128/205.12 |
| 4,770,169 | A * | 9/1988 | Schmoegner | A61M 16/08 128/206.24 |
| 6,041,777 | A * | 3/2000 | Faithfull | A61M 16/0054 128/200.24 |
| 6,631,717 | B1 * | 10/2003 | Rich | A61M 16/0045 128/204.18 |
| 8,720,439 | B1 * | 5/2014 | Kolkowski | A61M 16/16 128/203.12 |
| 2002/0094298 | A1 * | 7/2002 | Monagan | A61L 9/20 422/5 |
| 2002/0153010 | A1 * | 10/2002 | Rozenberg | A61M 16/0054 128/203.12 |
| 2003/0037790 | A1 * | 2/2003 | Brain | A61M 16/04 128/207.14 |
| 2003/0131844 | A1 * | 7/2003 | Kumar | A61K 33/00 128/200.24 |
| 2004/0047776 | A1 * | 3/2004 | Thomsen | A61L 2/10 422/186.07 |
| 2005/0133031 | A1 * | 6/2005 | Han | A61M 16/0808 128/204.17 |
| 2005/0163652 | A1 * | 7/2005 | Metzger | A61L 2/10 422/22 |
| 2005/0232825 | A1 * | 10/2005 | Fowler | A61L 9/20 422/121 |
| 2006/0272682 | A1 * | 12/2006 | Langford | A61B 1/123 134/42 |
| 2007/0163592 | A1 * | 7/2007 | Reinstadtler | A61M 16/0078 128/205.27 |
| 2008/0302364 | A1 * | 12/2008 | Garde | A61M 16/0045 128/204.23 |
| 2010/0122699 | A1 * | 5/2010 | Birnkrant | A61M 1/0023 128/204.21 |
| 2010/0242961 | A1 * | 9/2010 | Mougel | A61M 16/1055 128/203.16 |
| 2011/0165663 | A1 * | 7/2011 | Davis | F01N 3/04 435/266 |
| 2012/0160239 | A1 * | 6/2012 | Hingley | A61M 16/0045 128/201.25 |
| 2012/0234166 | A1 * | 9/2012 | Markham | A61L 9/20 95/214 |
| 2012/0298099 | A1 * | 11/2012 | Lalonde | A61M 16/0057 128/200.16 |
| 2014/0154134 | A1 * | 6/2014 | Leyva | A61M 16/06 422/28 |

OTHER PUBLICATIONS

"SoClean CPAP Sanitizer is the Innovative Health Care Gift of the Year," accessed on the Internet, Dec. 3, 2012. http://www.betterrestsolutions.com/sleep-talk/2012/12/03/soclean-cpap-sanitizer-is-the-innovative-health-care-gift-of-the-year/ (6 pages).

"SoClean CPAP Sanitizer Now Distributed by CareFusion," accessed on the Internet, Jan. 24, 2013. http://www.betterrestsolutions.com/sleep-talk/2013/01/24/soclean-cpap-sanitizer-now-distributed-by-carefusion/ (6 pages).

* cited by examiner

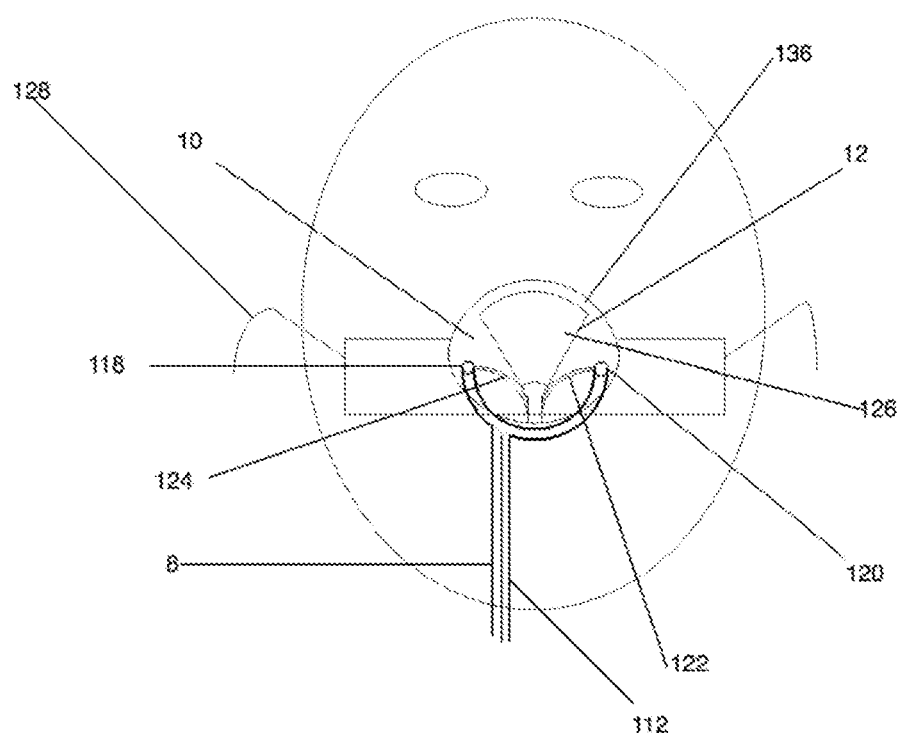

WATER AND AIR PRECONDITIONING APPARATUS

This disclosure generally relates to a gas and liquid preconditioning system. More specifically, the invention relates to a system used for delivering pretreated water and air to a CPAP machine. This invention claims priority to provisional patent application 61/654,382, filed Jun. 1, 2012 entitled "Water and Air Preconditioning Apparatus."

TECHNICAL FIELD

Background

Sleep apnea affects approximately 8% or 25 million adults in the US. As many as 4% of children and adolescents may be affected. The most common treatment of obstructive sleep apnea is the use of a continuous positive airway pressure (CPAP) machine. A CPAP machine delivers a continuous flow of pressurized air to a user's airway through the use of a facemask and a hose. Although CPAP therapy is a standard treatment for sleep apnea, patient compliance is a major challenge with CPAP users due to mask discomfort, air leak issues, and general ineffectiveness associated with CPAP machine use.

The CPAP machine may cause several issues for users. Some of these issues may include creating facemask discomfort, causing infections, allergies, and inadequately filtering particulates from the delivered air. In some cases, the CPAP facemask can cause a user discomfort by causing irritation on the bridge of the nose and on the forehead. Also, the CPAP machine generally requires frequent water replacement and cleaning. In some cases, daily water replacement is recommended if the CPAP machine incorporates a humidifier. Such a rigorous schedule of cleaning and water replacement can be tedious for most users. However, when the rigorous schedule is not maintained, the water in the CPAP machine may stagnate and allow for bacteria growth. The CPAP machine may create an environment for bacterial growth that subjects the user to sinus infections, upper airway infections, conjunctivitis, and ear infections. The CPAP machine also usually requires frequent filter changes that can be tedious and costly for a user. A lack of frequent filter changes, and a lack of bacterial/viral filtration, however, can lead to serious health implications since the CPAP machine supplies air directly to the patient. It is vitally important that air is properly filtered and disinfected so that allergens, viruses, and bacteria are not introduced to the patient by the CPAP machine.

The CPAP machine can also cause undesirable use conditions, known as "rainout" and "mouth leak." Rainout occurs when water collects in the hose and in the facemask transporting humidified air to the user. Water forms by condensation due to a temperature difference between the air in the hose and the surrounding room. Rainout causes a loss of humidification in the air being delivered to the user, which causes the air to be drier. Dry air can make a user congested, which then encourages the user to breath orally. Oral breathing, however, allows pressurized air to escape through the mouth, which is referred to as "mouth leak." Mouth leak can be problematic for CPAP users. As air escapes from the mouth, the CPAP machine compensates by increasing the airflow, which may cause dryness and irritation in the user's nasal mucosa.

SUMMARY

In one embodiment, a fluid preconditioning apparatus is used to pretreat fluids for an air disbursement machine. The fluid preconditioning apparatus includes a housing having a first portion, a second portion, and a partition member located between the first portion and the second portion. The first portion includes a first outlet for a treated gas, a second outlet for a treated liquid, a third outlet for a hose and a cover. The second portion includes a first inlet configured to receive a gas, a second inlet adapted to receive a liquid, a power supplying element, a gas treatment chamber mounted within the housing connecting to the first inlet, a gas flow generator for moving the gas from the first inlet through the gas treatment chamber and the first outlet, and may include an outlet for a hose. The second portion also includes a liquid treatment chamber disposed within the housing that connects to the second inlet, and a liquid flow generator for moving the liquid from the second inlet through the liquid treatment chamber and the second outlet. The gas treatment chamber creates the treated gas by filtering and disinfecting the gas and the liquid treatment chamber creates the treated liquid by filtering and disinfecting the liquid.

The fluid preconditioning apparatus may further comprise a gas treatment chamber including an ultraviolet (UV) ballast, a germicidal bulb, a power supply, a gas mover, and a controller for the gas mover and/or a liquid heating element. In one embodiment the gas blower may be an air blower.

In another embodiment the liquid treatment chamber can include a water pump, a UV light source and at least one liquid filter. The UV light source and liquid filter can disinfect and remove particulates from the liquid. The liquid treatment chamber may also include a liquid heating element and/or a humidification chamber.

The fluid preconditioning apparatus may treat a gas comprising oxygen, air, carbon dioxide, nitrogen, or any combination thereof. The gas may be an aerosol.

In another embodiment, the fluid preconditioning apparatus comprises a controller that includes at least one display to show liquid level within the humidification chamber and the liquid level within the liquid treatment chamber. The controller can include a user interface that allows a user to provide threshold values for the desired liquid level in the humidification chamber and the liquid treatment chamber. The threshold values prompt the controller to refill the chambers with a liquid.

Another embodiment includes a continuous positive airway pressure (CPAP) accessory system to pretreat fluids that are supplied to a CPAP machine and increase patient comfort and ease-of-use of a CPAP machine. The CPAP accessory system includes a fluid preconditioning apparatus comprising a housing having a first portion, a second portion, and a partition member located between the first portion and the second portion. The first portion includes a gas outlet for delivering a treated gas to a CPAP machine, a first liquid outlet for delivering a treated liquid to the CPAP machine, a second liquid outlet for delivering the treated liquid to CPAP system accessories, a tube outlet that connects to a hose sheath, and a cover. The second portion includes a first inlet configured to receive a gas, a second inlet adapted to receive a liquid, a gas treatment chamber disposed within the housing connecting to the first inlet, a gas flow generator for moving gas from the first inlet through the gas treatment chamber and the first outlet. Additionally, the second portion includes a liquid treatment chamber disposed within the housing that connects to the second inlet, at least one liquid heating element, and a liquid flow generator for moving the liquid from the first liquid inlet through the liquid treatment chamber and the second liquid outlet. The gas treatment chamber creates the treated gas by filtering and disinfecting the gas, and the liquid treatment chamber creates the treated liquid by filtering and disinfecting the liquid. The hose sheath comprises a flexible hose with a main lumen, and at least one flexible tube coupled to the flexible hose along one of the exterior wall and the interior wall of the flexible hose. One end of the flexible tube is coupled to the fluid preconditioning apparatus and the other end of the flexible tube is coupled to a mask pad. The flexible tube transports the heated liquid along the wall of the flexible hose for a predetermined distance from the fluid preconditioning apparatus to a mask pad. The mask pad is disposed adjacent to a CPAP facemask. The mask pad includes a pouch portion with an inlet port and an outlet port, a first fluid delivery tube that couples to the inlet port and a second fluid delivery tube that couples to the outlet port. The first fluid delivery tube moves the heated fluid from the fluid preconditioning apparatus to the pouch portion and the second fluid delivery tube returns the heated fluid back to the fluid preconditioning apparatus.

The CPAP accessory system may include a gas treatment chamber comprising an ultraviolet (UV) ballast, a germicidal UV bulb, a power supply, a gas mover, and a controller for the gas mover. The gas treatment chamber may comprise a liquid heating element.

The CPAP accessory system may treat oxygen, air, carbon dioxide, nitrogen, or any combination thereof. The gas may be an aerosol.

In another embodiment, the CPAP accessory system can have a liquid treatment chamber comprising a water pump, a UV light source, and at least one liquid filter. The liquid filter is used to remove particulates from the liquid. The liquid treatment chamber may also include a liquid heating element and/or a humidification chamber.

In another embodiment the CPAP accessory system may further comprise a controller that includes at least one display to show liquid level within the humidification chamber and the liquid level within the liquid treatment chamber. The controller can include a user interface that allows a user to provide threshold values for the desired liquid level in the humidification chamber and the liquid treatment chamber, wherein the threshold values prompt the controller to refill the chambers with a liquid.

The CPAP accessory system may further comprise a second flexible tube with a lumen that is able to accommodate the outer diameter of the flexible hose. The flexible tube may comprise a hose sheath and multiple lumens wherein at least one lumen is able to accommodate a CPAP hose.

In still another embodiment, the mask of the CPAP accessory system comprises a double adhesive material and a tacky material on one side. The mask pad may also comprise one or more straps for better securing the mask pad to a user's face. The mask pad may further comprise a nasal dilator.

The nasal dilator of the CPAP accessory system may include two pads, a pushing element, and an adjustment element wherein the pads are coupled to the pushing element and the pushing element is coupled to the adjustment element.

A method to precondition a gas and a liquid delivered to a CPAP machine includes receiving the gas and the liquid, filtering at least one of the gas and the liquid, disinfecting at least one of the gas and liquid, and delivering at least one of a treated gas and a treated liquid to a CPAP machine that resides within a compartment of the fluid preconditioning apparatus. The treated gas has been filtered and disinfected and the treated liquid has been filtered and disinfected. The method may include treating the gas by filtering, disinfecting, and humidifying. Further, moving the gas through at least one air filter and moving the liquid through at least one liquid filter may filter the gas and liquid. Exposing the gas to a UV light source and exposing the liquid to a UV light source may disinfect the gas and the liquid.

Another method includes insulating the CPAP hose within a flexible sheath to prevent condensation. The CPAP hose is enclosed by a flexible sheath that contains a spiraling flexible tube. The spiraling flexible tube encircles the CPAP hose. A heated liquid is delivered through the spiraling flexible tube to warm the lumen of the flexible sheath. The method further includes providing cushioning, heat, and nasal dilation to a CPAP user's face using a mask pad that is placed between the user's face and the CPAP facemask. This involves delivering the heated liquid to the mask pad, filling the pouch of a mask pad having a gelatinous outer portion with the heated liquid and applying force using two nasal pads pressed against a user's face and pushing away from the user's nose. The method also includes preconditioning a gas and a liquid delivered to a continuous positive airway pressure CPAP machine by receiving the gas and the liquid, filtering at least one of the gas and the liquid, disinfecting at least one of the gas and liquid, and heating at least one liquid.

The method also includes transferring fluids to a CPAP machine and CPAP accessories by delivering at least one of a treated gas and a treated liquid to a CPAP machine that resides within a compartment of the fluid preconditioning apparatus. The treated gas has been filtered and disinfected and the treated liquid has been filtered and disinfected. The method of transferring fluids also includes delivering at least one heated liquid to the CPAP hose and the mask pad and retrieving cooled liquid from the CPAP hose and mask pad. The cooled liquid is re-heated and continues a cycle of being delivered back to the CPAP hose and the mask pad. The gas may be further humidified, filtered, disinfected, or combinations thereof. Filtering the gas and liquid may include moving the gas through at least one air filter and moving the liquid through at least one liquid filter. A disinfecting element may include exposing the gas to a UV light source and exposing the liquid to a UV light source.

BRIEF DESCRIPTION OF THE DRAWINGS

The accompanying drawings illustrate various embodiments of the present disclosure and are a part of the specification. The illustrated embodiments are merely examples and do not intend to be limiting.

FIG. 13 shows a perspective view of a mask pad.

DETAILED DESCRIPTION

The following description is meant to be illustrative only and not limiting. Other embodiments of this disclosure will be apparent to those of ordinary skill in the art in view of this description.

Figure 1:
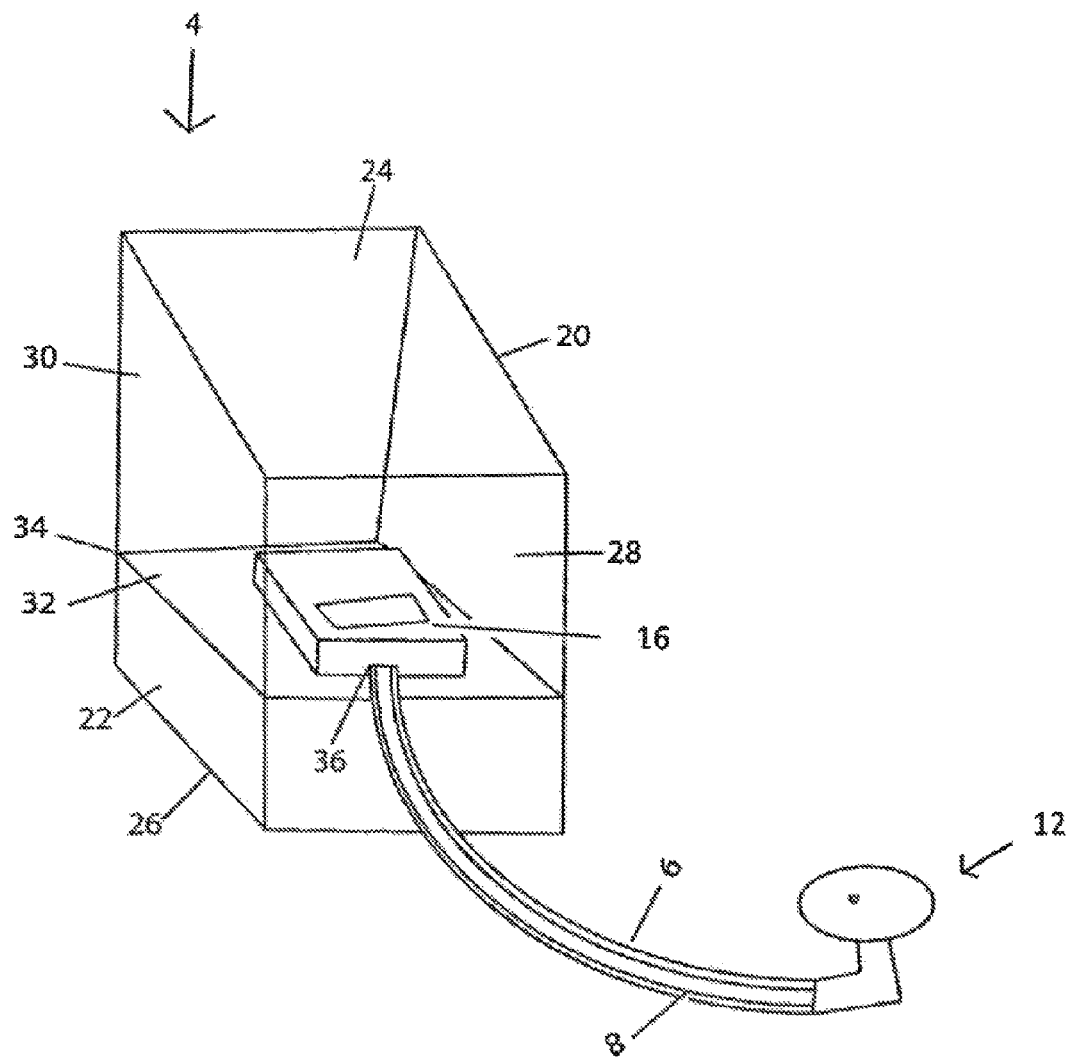
FIG. 1 illustrates a schematic view of a fluid preconditioning apparatus.

FIG. 1 shows a schematic view of a fluid preconditioning apparatus 4. The fluid preconditioning apparatus 4 is configured to work with a hose sheath 6 and a mask pad 12. The fluid preconditioning apparatus 4 is configured to retain a CPAP machine within an enclosed compartment. The fluid preconditioning apparatus 4 can have at least one aperture 36 to allow the hose sheath 6 to pass through the enclosed compartment. The hose sheath 6 has a proximal end, a distal end, and a main lumen. The proximal end of the hose sheath 6 can be coupled to the fluid preconditioning apparatus 4 and the distal end can be coupled to the mask pad 12. In some embodiments, the mask pad 12 can be coupled to a nasal dilator 14, wherein the nasal dilator 14 is used in conjunction with the mask pad 12.

The fluid preconditioning apparatus 4 can provide pretreated air and pretreated water to a CPAP machine, ensuring that clean air and water are delivered to the user. The fluid preconditioning apparatus 4 continuously treats the water and air, thus reducing the number of water and filter changes typically required for the CPAP machine. The fluid preconditioning apparatus 4 may also increase the comfort of using a CPAP machine by providing a cushion for the user's facemask and reducing condensation in the hose 8 and facemask 10 by insulating the hose 8.

The fluid preconditioning apparatus 4 may be used in some embodiments as a stand-alone device. Alternatively, in other embodiments, the fluid preconditioning apparatus 4 may be used in combination with a CPAP machine. In various embodiments, the fluid preconditioning apparatus 4 is used to pretreat one or more fluids, wherein the fluid includes either a gas or a liquid. Examples of a gas include, but are not limited to, oxygen, air, carbon dioxide, nitrogen, or any combination thereof. Examples of a liquid include, but are not limited to, water and medicated liquids, such as a bronchodilator. Subsequent paragraphs discussing embodiments that refer to air and water embodiments may include, whenever applicable, these other types of gases and liquids. In various embodiments, the fluid preconditioning apparatus 4 pretreats one or more fluids that are provided to a CPAP machine, or other similar respiratory machines that deliver respiratory fluids to a person. The fluid preconditioning apparatus 4 pretreats a fluid, in some embodiments, by removing particulates, disinfecting, and/or heating the fluid. In some embodiments, pretreatment of a gas includes humidification of the gas.

The fluid preconditioning apparatus 4, includes a top portion 20 and a base portion 22. In some embodiments, the fluid preconditioning apparatus 4 can have an upper side 24, a lower side 26, a front side 28, a back side 30, and lateral walls 32 between the upper side 24 and lower side 26 defining an interior compartment. In such embodiments, the interior compartment can divided into two enclosed compartments that make up the top portion 20 and the base portion 22. It is understood that a compartment includes the walls/surfaces defining the space of the compartment. The top portion 20 and the base portion 22 are separated by a partition 34. The top portion 20 is a compartment configured to provide an enclosure for a CPAP machine 16 and to provide preconditioned fluids to the CPAP machine 16.

A hose sheath 6 may be connected to the fluid preconditioning apparatus 4. In some embodiments, the spiral or coaxial lumens of the hose sheath 6 are coupled to a cuff 40 or other similar connector. The cuff may be connected to a supply tube and valve that delivers heated fluids from the base portion 22 of the fluid preconditioning apparatus 4. In other embodiments, the cuff 40 may be connected to a supply tube that delivers heated fluids, such as heated water, from an external reservoir 44.

Figure 2:
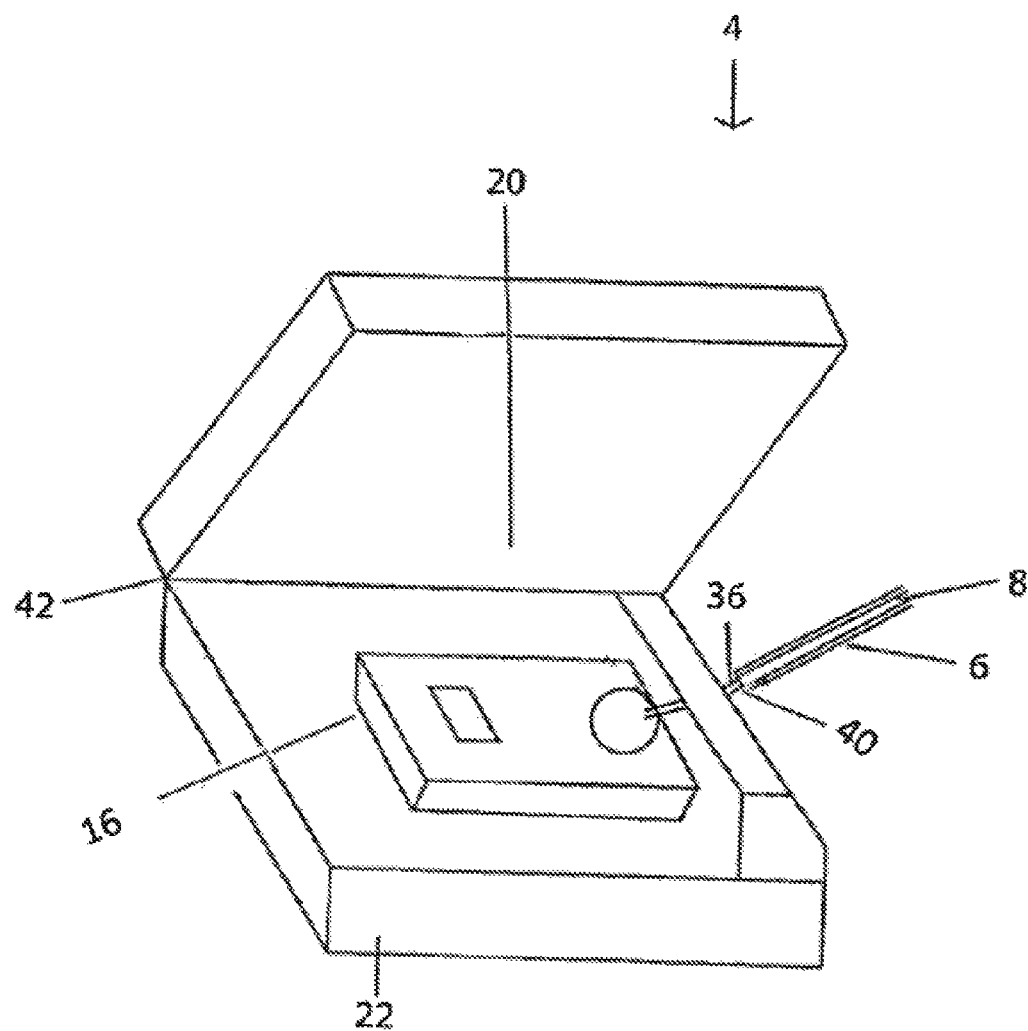
FIG. 2 shows a perspective view of an embodiment of the fluid precondition machine.

FIG. 2 shows a perspective view of an embodiment of the fluid preconditioning apparatus 4 retaining a CPAP machine 16 within the top portion 20 with a hose sheath 6 attached through the top portion 20. In other embodiments, the hose sheath may be attached through the bottom portion 22. In various embodiments, the CPAP machine 16 can be positioned within an enclosed top portion 20 of the fluid preconditioning apparatus 4, wherein at least a portion of a wall of the top portion 20 can be coupled to the base portion 22 by a hinge 42 or another similar connecting element. In some of these embodiments, only portions of the top portion 20 are decouplable from the base portion 22 with the remaining portions of the top portion 20 being permanently affixed to the base portion 22. In other embodiments, the walls of the top portion 20 can be fully decouplable from the base portion 22. In yet other embodiments, the top portion 20 can be coupled to the base portion 22 by a sliding element. The sliding element moves the top portion 20 horizontally across the base portion 22 to provide an opening for a user to insert or remove a CPAP machine 16 into the top portion 20 enclosure. In some embodiments, the top portion 20 only partially covers the CPAP machine. In other embodiments, the top portion 20 is not an enclosure, as it does not cover any portion of a CPAP machine.

In some embodiments, the top portion 20 can have at least one aperture 36 that allows passage of the CPAP hose 8 alone or through a connector cuff 40, or other similar annular-connecting element, coupling the hose sheath 6 to the top enclosure aperture 36. When using the hose sheath 6, the CPAP hose 8 can be inserted into the hose sheath 6 that is coupled to the cuff 40 to pass through the top enclosure aperture 36.

In other embodiments, the top portion 20 can have at least one aperture 36 that allows passage of the hose sheath 6 alone or through a connector cuff 40, or other similar annular-containing element that can couple the hose sheath 6 to an aperture 36.

The base portion 22 is the interior compartment that pretreats fluids. In various embodiments, the base portion 22 has one or more exterior air vents 38 along portions of the lateral walls 32, allowing untreated air to enter into the base portion 22. The base portion 22 and top portion 20, according to some embodiments, may be made from glass, a metal, a plastic material, or any combination thereof. In some embodiments, a portion of the top portion 20 is made of a clear material, for example, clear polycarbonate or glass, to allow a user to visually detect the CPAP machine 16 and the CPAP machine features, for example, the water level of the CPAP machine 16.

Untreated water and air are introduced into the base portion 22 of the fluid preconditioning apparatus 4, the mechanisms for which will be discussed in greater detail in subsequent paragraphs. In some embodiments, the water and air are pretreated when each fluid passes through one of a filtering element, disinfecting element, a heating element, or any combination thereof. Once pretreated, the water and air exit the base portion 22 and enter into the top portion 20 of the fluid preconditioning apparatus 4 and are delivered to the CPAP machine that resides in the top portion 20. The mechanism of delivery will also be discussed in later sections. In some embodiments, a portion of the pretreated water is delivered to one or more accessories that may include the hose sheath 6 and/or the mask pad 12. The pretreated water delivered to the accessories will return back to the base portion 22 to be pretreated again. In other embodiments, the top portion 20 only partially covers the CPAP machine 16. In still other embodiments, the top portion 20 is not an enclosure because it does not cover any portion of the CPAP machine 16.

Figure 3:
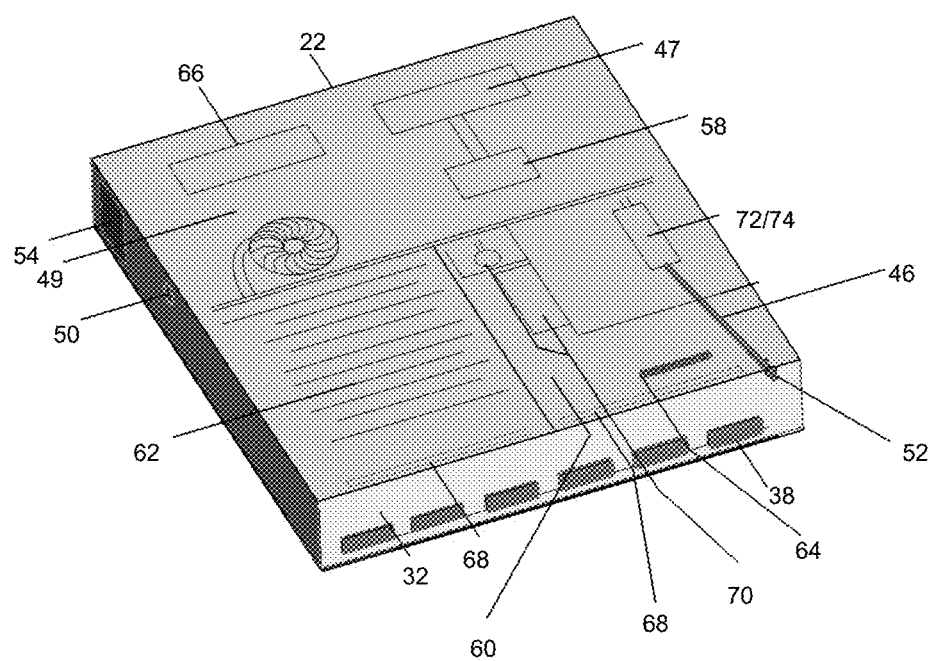
FIG. 3 shows a sectional view of the base portion of the fluid preconditioning apparatus.

FIG. 3 illustrates the base portion 22 of the fluid preconditioning apparatus 4 in accordance with some embodiments. The base portion 22 receives untreated fluids. In various embodiments, the base portion 22 can include a gas inlet 50, a liquid inlet 52, a power supplying element 54, a gas treatment chamber 49, a gas flow generator for moving gas, a power controller 47, a gas flow generator controller 58, a liquid treatment chamber 60, and a liquid flow generator. The liquid treatment chamber 60 may also include a liquid heating element 68. In some of these embodiments, the untreated air enters in through a gas inlet configured to receive gas, for example, one or more exterior air vents 38 or openings, along the lateral walls 32 of the base portion 22. In some embodiments, untreated water enters the base portion 22 through a liquid inlet 52, for example, a water inlet tube 46 connected to an exterior water reservoir (not shown in figures) or a water inlet tube connected to the CPAP water reservoir (not shown in figures). In other embodiments, the untreated water is added into a reservoir compartment within the base portion 22. Once the water and air enter the base portion 22, the components within the base portion 22 act to pretreat the fluids.

In various embodiments, power is delivered to components within the base portion 22 by a power supplying electrical element 54. Examples of a power supplying electrical element 54 may include, but are not limited to, a power plug or one or more batteries coupled to the electrical components within the system for providing power to treat fluids.

In some embodiments, the gas flow generator includes one or more air blowers 56, or similar type of equipment. In other embodiments, as shown in FIG. 3, the gas flow generator also includes a controller 58 and a separate power supplying controller 47 for regulating or adjusting the one or more air blowers 56. The gas flow generator pulls air into the base portion 22, moves the air through the gas treatment chamber 49, and delivers the air to the top portion of the fluid preconditioning apparatus 4.

In other embodiments, the gas treatment chamber 49 can include one or more air particulate filters 62. Examples of air particulate filters 62 include, but are not limited to, ultra fine air filter or a standard HEPA filter. In other embodiments, the gas treatment chamber 49 includes at least one disinfecting element, for example, an ultraviolet (UV) light source 64 or bacteria air filter (not shown in figures). In some of these embodiments, a UV ballast 66 is added to limit the amount of current provided to the UV light source 64. In other embodiments, the gas treatment chamber includes a heating element 68 to heat air. In other embodiments, the gas treatment chamber 49 includes a humidifier for humidifying the air being supplied to a CPAP machine. Some CPAP machines do not have a humidification capability. In the various embodiments described herein, the gas treatment chamber 49 may be used to filter particulate from the air, and disinfect, heat, and humidify the air prior to delivering the air to the CPAP machine.

In other embodiments, the liquid flow generator includes one or more liquid pumps, for example, a peristaltic pump 70, or other similar equipment. The liquid flow generator pulls water, for example, into the base portion 22 through a liquid inlet 52, moves water through the liquid treatment chamber, and delivers the water to the CPAP machine.

Figure 4:
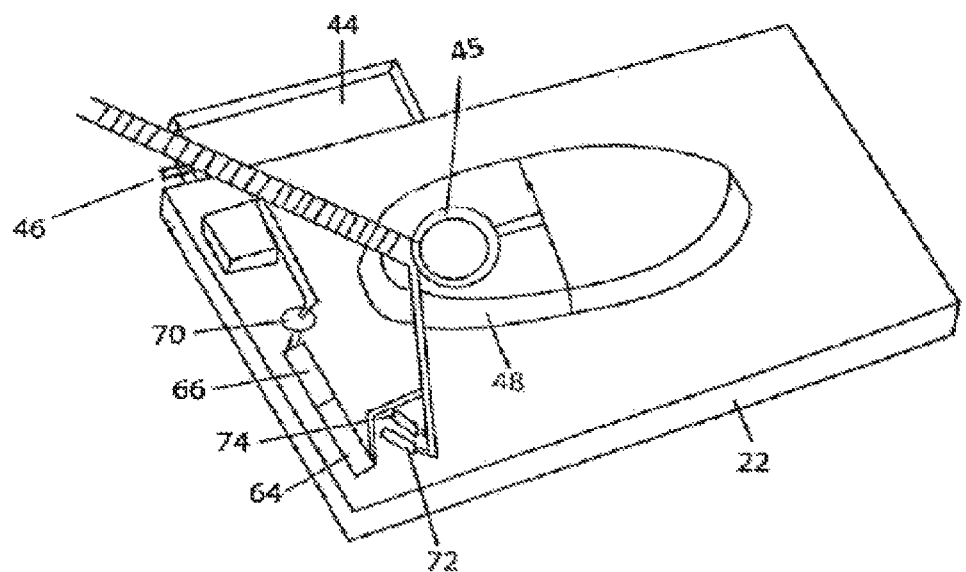
FIG. 4 illustrates a perspective view of the fluid preconditioning apparatus.

In some embodiments, as shown in FIG. 4, the liquid treatment chamber can include a particulate filtering element, for example, a hollow membrane fiber filter 72, a sediment filter 74, and/or a reverse osmosis filter (not shown in figures). In other embodiments, the liquid treatment chamber can include a disinfecting element, for example, a UV light source 64 or a bacteria filter (not shown in figures). In various embodiments described herein, the liquid filter may be used to remove particulates from and disinfect the water prior to delivering the water to the CPAP machine 16.

In some embodiments, a set of switches (not shown in figures) may be constructed into the base portion 22 to control the blower 56, pumps 70, UV light 64, and any other electrical component. In some embodiments, the set of switches may be configured to allow a user to adjust temperature regulation settings for the water being heated and supplied to the CPAP machine and/or accessories.

FIG. 4 illustrates a deconstructed fluid preconditioning apparatus 4. The fluid preconditioning apparatus 4 has a particulate filter 62 (FIG. 3), membrane fiber filter 72, sediment filter 74, and/or a reverse osmosis filter (not shown). In alternative embodiments, the fluid preconditioning apparatus 4 includes a disinfecting element, for example, a UV light source 64 and/or a UV ballast 66. In other embodiments the liquid filter may be used to remove particulates from and disinfect the water prior to delivering the water to the CPAP machine 16, and in particular, to the water reservoir 48 of the CPAP machine 16. At least one tubular member may deliver the treated water or other fluid to the CPAP water reservoir 48. The water or other liquid from the CPAP water reservoir/humidifying chamber 45 may be used to humidify the air provided through the CPAP hose 8.

Figure 5:
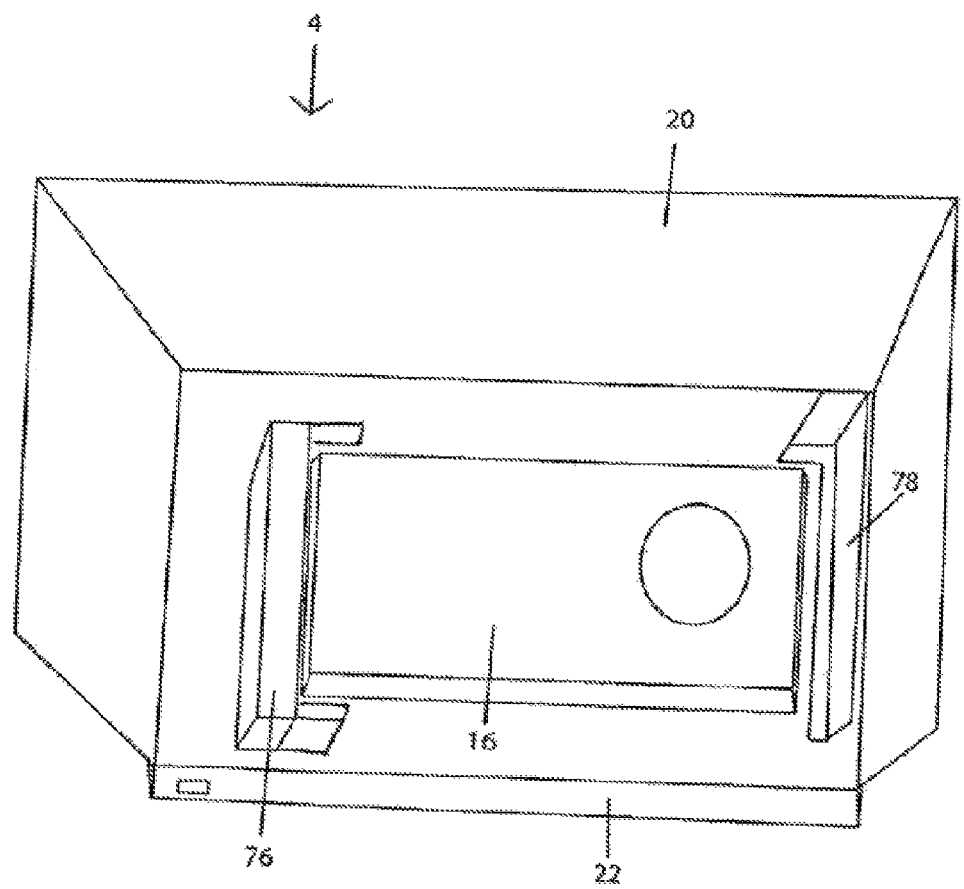
FIG. 5 illustrates an alternative perspective view of the fluid preconditioning apparatus.
Figure 6:
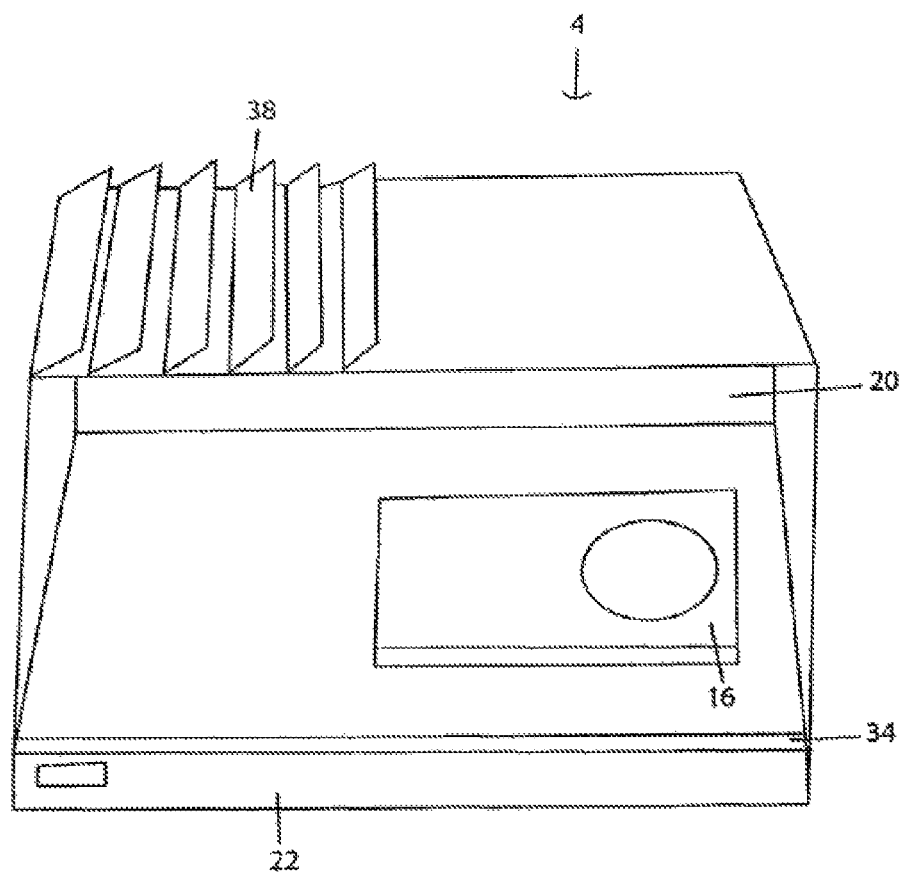
FIG. 6 is a side view of the fluid preconditioning apparatus.

FIGS. 5 and 6 show sectional and perspective views of the top portion 20 of the CPAP fluid preconditioning apparatus 4. The top portion 20 includes an enclosure, at least one air inlet vent 76 and a CPAP machine 16 that rests atop the partition 34 and above the base portion 22. The air inlet vent 76 can be designed to optimize how air flows into the CPAP machine. In various embodiments, the air inlet vent 76 directs air treated by the base portion 22 to the CPAP machine 16. In some examples the air inlet vents 76 may be designed to direct air in one or more directions within the top portion 20. In this embodiment, the air inlet vent 76 directs air in three directions: directly into the front end and portions of the adjacent sides of the CPAP machine 16. In other examples, air inlet vents 76 may be placed along one or more sides of the CPAP machine. In some embodiments, the top portion 20 is enclosed while in other embodiments the top portion 20 is not enclosed. In various embodiments, the top portion 20 includes one or more outlet air vent 78 and/or one or more exterior air vent 38. The outlet air vent 78 and exterior air vent 38 may assist in directing the flow of air to the CPAP machine 16 and prevent air pressure buildup in an enclosed top portion 20.

Figure 7:
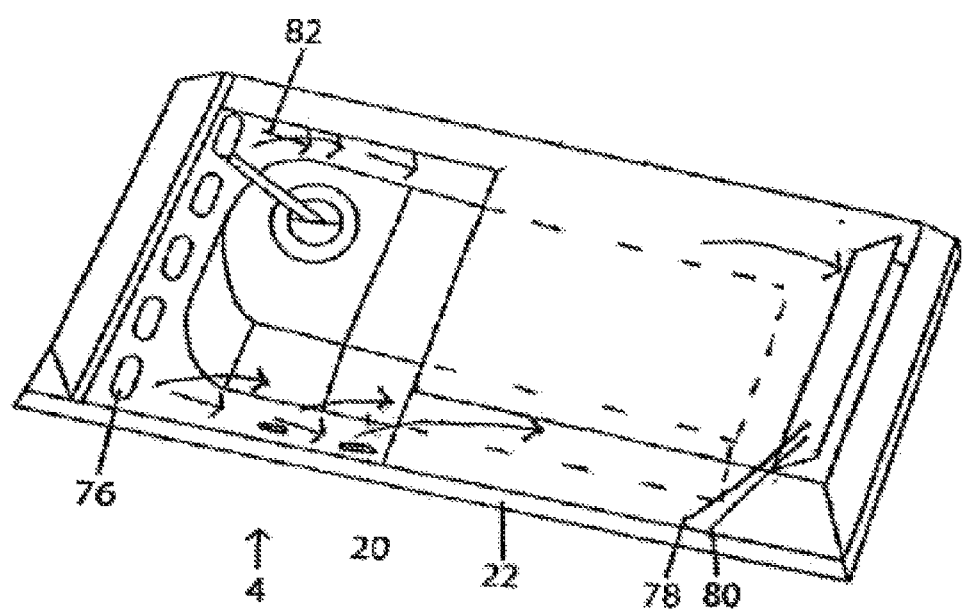
FIG. 7 illustrates an expanded view of the top portion of the fluid preconditioning apparatus.

FIG. 7 shows a perspective view of the fluid preconditioning apparatus 4 showing airflow 82 through the top portion 20. As shown in these figures, in certain embodiments the top enclosure 20 may include a plurality of air inlet apertures 76 and one or more outlet apertures 78 using a venting structure 80 disposed on the partition 34. Airflow 82 from the base portion 22 enters the top portion 20 via the air inlet apertures 76 through the partition 34 and then returns back into the base portion 22 through the air outlet aperture 78. In some embodiments, the air inlet and/or outlet apertures 76, 78 are disposed directly in the partition 34. In other embodiments, the air inlet and/or outlet apertures 76, 78 are configured with particular venting structure 80 so as to direct airflow 82 in a particular direction.

Figure 8:
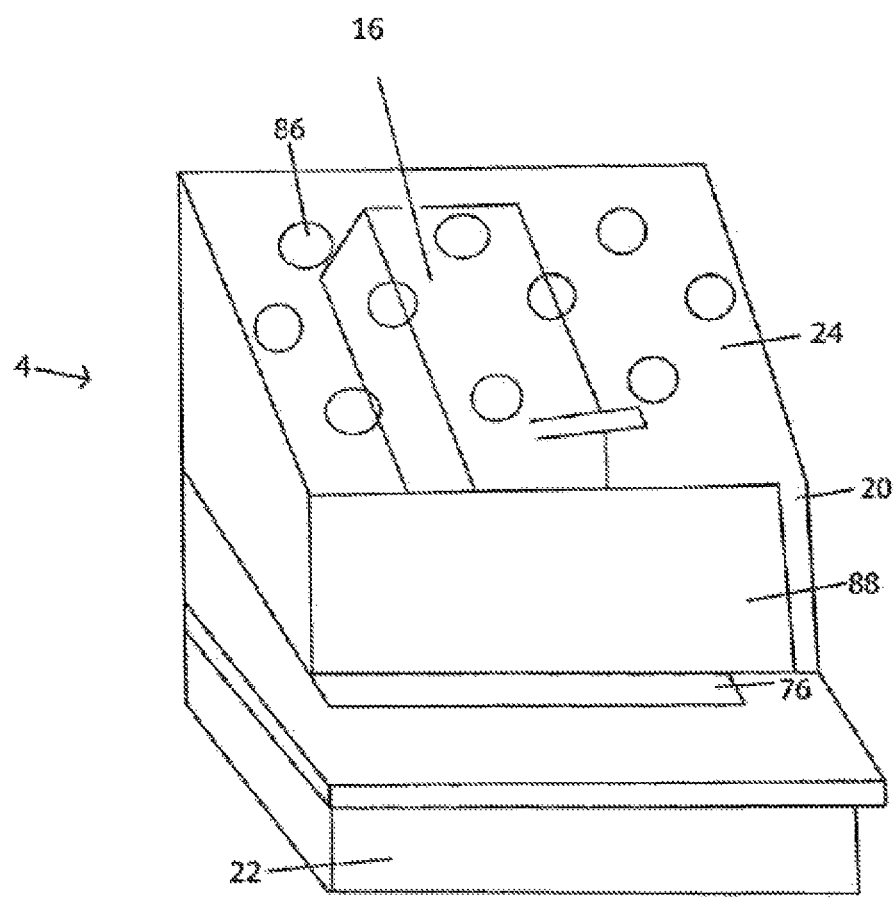
FIG. 8 illustrates the top portion of the fluid preconditioning apparatus.

FIG. 8 is a perspective view of a top portion cover of the fluid preconditioning apparatus 4, in some embodiments. This figure shows an enclosed top portion 20 with an upper side 24 that has been configured with an air channeling partition 84 (FIG. 9) having a plurality of upper side 24 apertures 86 that creates a passageway to direct inlet air from the base portion 22 into the top portion 20.

Figure 9:
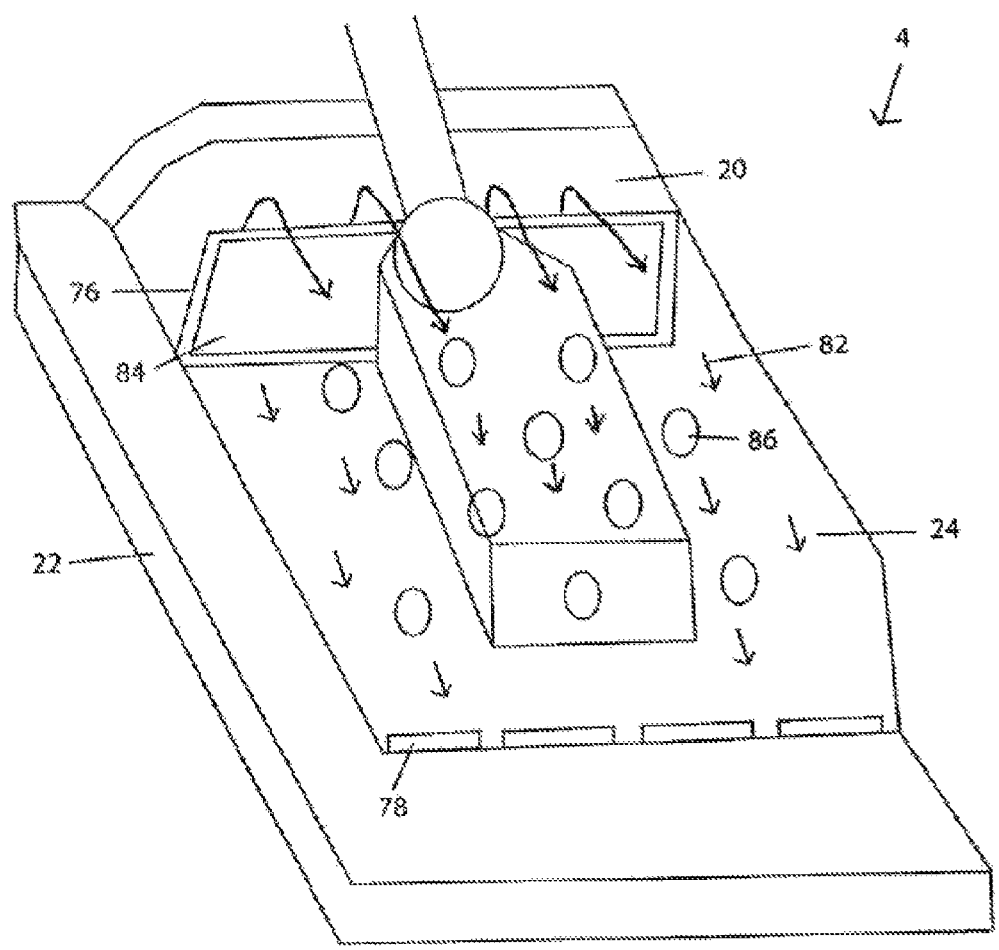
FIG. 9 shows another expanded view of the top portion of the fluid preconditioning apparatus.

FIG. 9 shows airflow 82 through the upper side 24 of the top portion 20, in some embodiments. The fluid preconditioning apparatus 4 includes the top portion 20, one or more air inlet apertures 76, one or more air outlet apertures 78, an air channeling partition on the front side 88 of the fluid preconditioning apparatus 4. Air enters through the one or more air inlet apertures 76 into the passageway contained within the upper side 24, enters the top portion 20 through the upper side apertures 86, and exits out the one or more air outlet apertures 78. Top portion 20 may have an upper side 24 with an air channeling partition 84 with a plurality of upper side apertures 86 that create a passageway to direct inlet air from the base portion 22 into the top portion 20.

Figure 10:
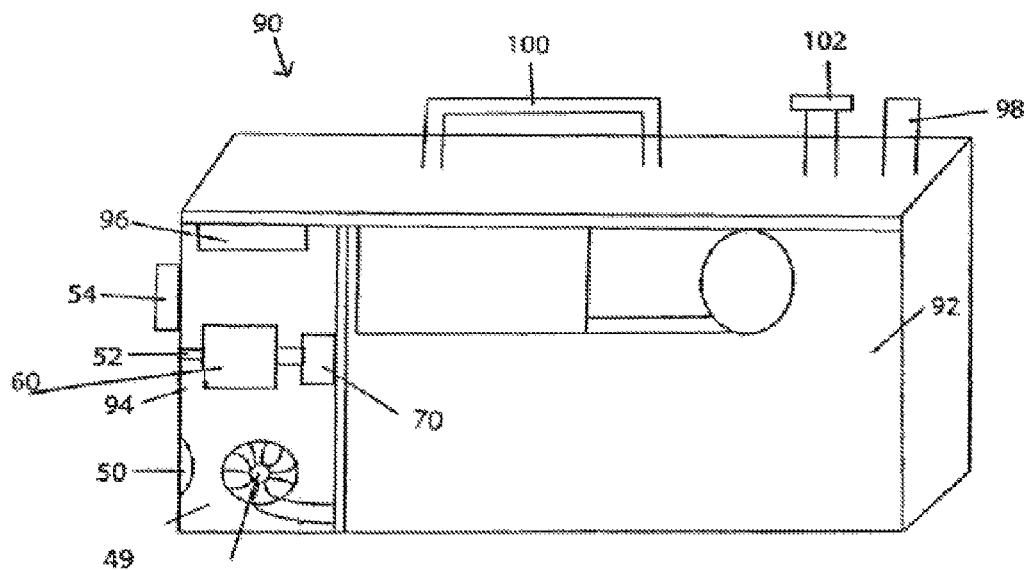
FIG. 10 shows a side view of the fluid preconditioning apparatus.

FIG. 10 is a perspective view of a portable fluid preconditioning apparatus 90, according to some embodiments. The figures show the portable fluid preconditioning apparatus 90 including an enclosed preconditioning portion 92, an enclosed storage portion 94, an outlet connector 98, and a handle 100. The portable gas preconditioning apparatus 90 may include a handle 100 to aid with device portability. In some embodiments, the portable fluid preconditioning apparatus 90 is configured to treat a gas, for example, but not limited to, air, nitrogen, and oxygen. In some of these embodiments, the storage portion 94 may include an outlet vent 96 to release excess air and prevent pressure buildup in the portable fluid preconditioning apparatus 90. In other embodiments, the portable fluid preconditioning apparatus 90 is configured to treat a liquid, for example, but not limited to, water or medicated liquids. The portable fluid preconditioning apparatus 90 enables a user to treat and store a fluid in a transportable container.

In some embodiments, the preconditioning portion 94 may be configured to treat a gas and comprises a gas inlet 50, a power supplying electrical element 54, a gas treatment chamber 49, a gas flow generator controller 58 for moving gas. Alternatively, the preconditioning portion 94 may be configured to treat a liquid and comprise a liquid inlet 52, a power supplying electrical element 54, a liquid treatment chamber 60, and a liquid flow generator pump(s) 70. The liquid or gas flow generator pump or controller 70, 58 delivers the liquid or the gas from the preconditioning portion 94 to the storage portion 92. The treated gas or liquid remains in the storage portion 92 until released via the outlet connector 98. A CPAP facemask and hose 8, or other similar apparatus, may be connected to outlet connector 98 to deliver treated air to a user.

Figure 11:
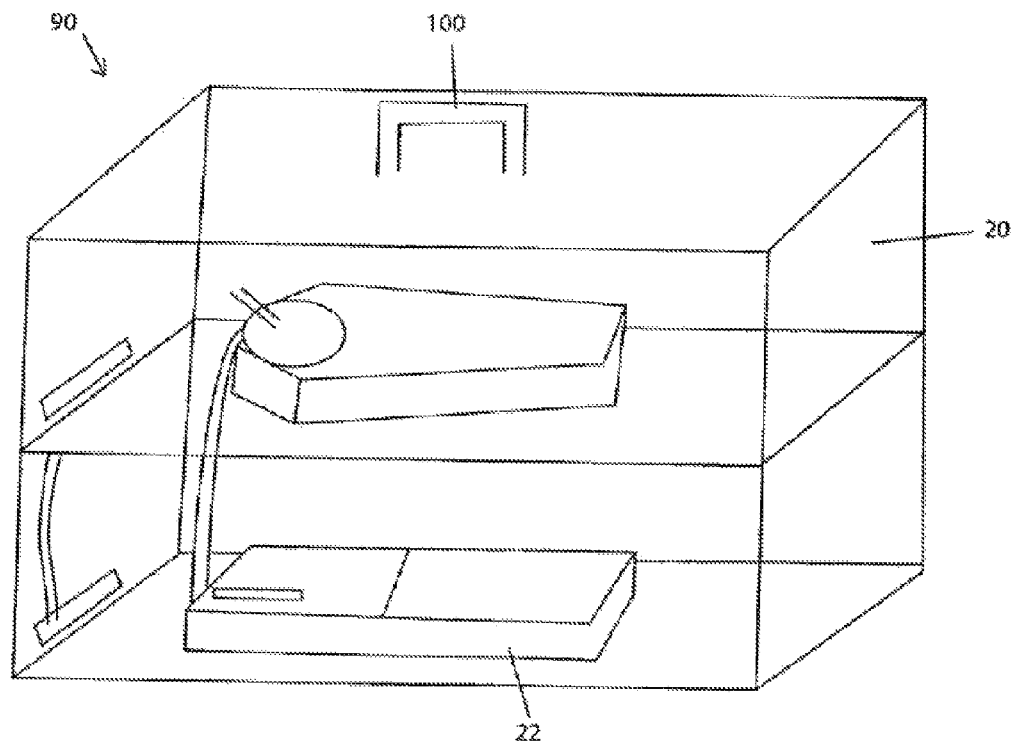
FIG. 11 illustrates a perspective view of a portable fluid preconditioning apparatus.

FIG. 11 is a perspective view of an example embodiment of the portable fluid preconditioning apparatus 90 that includes a top portion 20 and a base portion 22, similar to the fluid preconditioning apparatus 4 discussed in previous sections. In these embodiments, the portable fluid preconditioning apparatus 90 has a handle 100 attached to the outer portion of the portable fluid preconditioning apparatus 90. Also, the size of the top and base portions 20, 22 may be minimized to increase ease of travel and transportation.

Figure 12A:
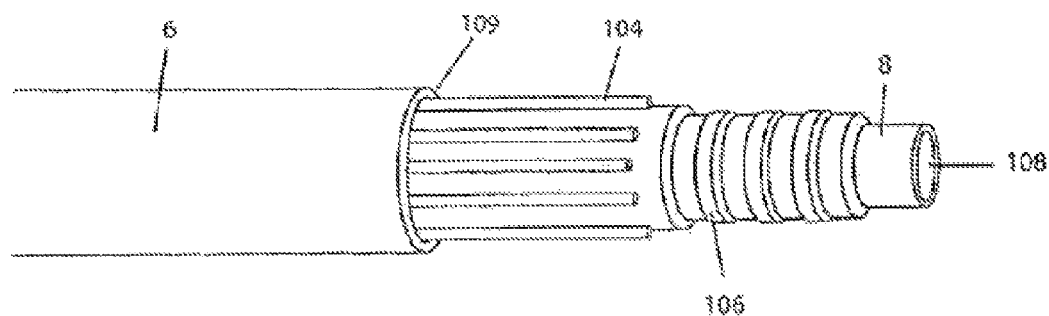
FIGS. 12A-B show various embodiments of a deconstructed hose sheath.
Figure 12B:
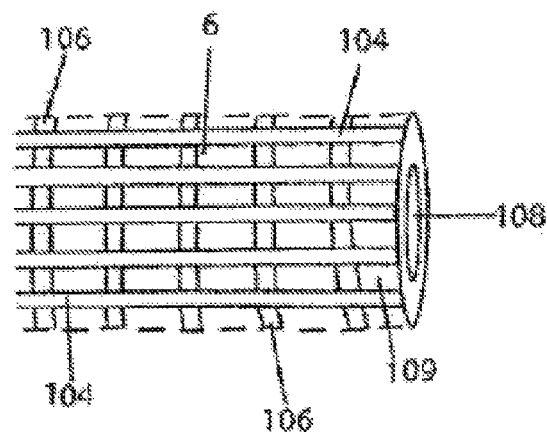

FIGS. 12A and 12B show a perspective view of a hose sheath 6, in various embodiments. In some embodiments, as shown in FIG. 12A, the hose sheath 6 is a flexible tube that comprises a main lumen 109 to hold and insulate a standard CPAP hose 8 for a given predetermined distance from the fluid preconditioning apparatus 4 and the CPAP facemask. In some embodiments, as shown in FIG. 12B, the hose sheath 6 may comprise a combination of coaxial tube 104 and spiraling tube 106 that encircle the main lumen 108 of the CPAP hose. These embodiments illustrate that both coaxial tube 104 and/or spiraling tube 106 may be used to transport a warm fluid along the wall of the hose sheath 6. Alternatively, just coaxial tube(s) 104 may be used, or just spiraling tube(s) 106 may be used.

In some embodiments, the hose sheath 6 comprises a lumen 109 and a single spiraling tube 106 coupled along the lumen 109 of the hose sheath. In various embodiments, the hose sheath 6 may comprise multiple spiraling tubes 106 along the outer or inner wall of the hose sheath 6. The spiraling tube 106 carries a warm fluid, such as heated water or air, along the hose sheath 6 from the fluid preconditioning apparatus 4 to the CPAP facemask 10. Condensation inside the standard CPAP hose 8 may be reduced by insulating the CPAP hose 8 with the heated fluid traveling along the spiraling tube 106 of the hose sheath 6. In some embodiments, the hose sheath 6 may have separate spiraling tubes 106 that return the fluid back from the CPAP facemask to the fluid preconditioning apparatus 4. In other embodiments, the spiraling or coaxial tubes 106, 104 of the hose sheath 6 may be heated electrically with, for example, a heated wire traveling inside of the spiraling or coaxial tubes 106, 104.

FIG. 13 is a perspective view of a mask pad 12 in relation to a CPAP facemask 10, in accordance with some embodiments. In some embodiments, the mask pad 12 comprises a hollow pouch 126 made of a flexible and soft material, an outlet port 118, an inlet port 120, an inlet delivery tube 122 that couples to the inlet port 120 and a outlet delivery tube 124 that couples to the outlet port 118. In various embodiments, the hollow pouch 126 may be filled with a liquid, such as heated water or gas. The inlet and outlet tubes 122, 124 couples to the hollow pouch 126 via the inlet port 120 and an outlet port 118 to circulate a heated fluid into and out of the mask pad 12. Examples of a flexible and soft material include, but are not limited to, silicone, urethane, and polypropylene.

In some embodiments, a warm fluid is supplied to the CPAP facemask 10 by an inner lumen tube 112. The inner lumen tube 112 travels inside the lumen of a standard CPAP hose 8 and travels up to the mask pad 12 and couples to the inlet port 120. In these embodiments, one end of the inner lumen tube 112 resides inside the CPAP machine and the other end of the inner lumen tube couples to the inlet port 120 of the mask pad 12. In some embodiments, the outlet delivery tube 124 couples to the spiraling or coaxial tubes 106, 108 of the hose sheath 6, as illustrated in FIGS. 12A-B, and return the warm fluid back to the base portion 22 of the fluid preconditioning apparatus 4 or an external reservoir.

Alternatively, in other embodiments, the mask pad 12 comprises a hollow pouch 126, a heating element 136, an inlet port 120, and outlet port 118. The hollow pouch 126 covers the heating element 136, which enters the mask pad 12 through the inlet port 120 and exits out the outlet port 118. In some embodiments, the heating element 136 will travel through the hose sheath 6 and connect to the mask pad 12. In other embodiments, the heating element will be a stand-alone device (not shown in figures) coupled to the mask pad 12, having a positive and negative terminal extending to a battery pack pouch supported by the hollow pouch (not shown in figures). Examples of heating elements include, but are not limited to, electrically conductive wires and/or wire assemblies.

In various embodiments, the mask pad 12 is positioned between the CPAP facemask and the user's face. In some of these embodiments, the mask pad 12 contacts that patient face across the nose and portions of the cheek adjacent to the nose. In other embodiments the mask pad 12 may contact a CPAP user on the bridge of the nose, cheek areas adjacent to the nose, and portions of the forehead.

The various locations on the face target different paranasal sinuses. The sinus sphenoidalis and cellulae ethmoidales are located approximately around the bridge of the nose. The sinus maxillaris is located approximately at the cheek areas adjacent to the nose. The sinus frontalis is located approximately at the forehead area.

In some embodiments, the mask pad 12 may include an adhesive portion that secures the mask pad 12 on a user's face during use. In other embodiments, a portion of the mask pad 12 may comprise a material having a tacky surface to increase securement of the mask pad 12 against the user's face. An example of a material with a tacky surface includes, but is not limited to, a silicone rubber.

In some embodiments, as shown in these figures, the mask pad 12 may be secured to a user's face by one of more straps 128 that wrap behind the CPAP user's head. In some of these embodiments, head straps 128 pull the mask pad 12 towards the back of the head and cause the skin around the user's nose to move towards the ears, which may encourage fuller breathing in a CPAP user.

Figure 14:
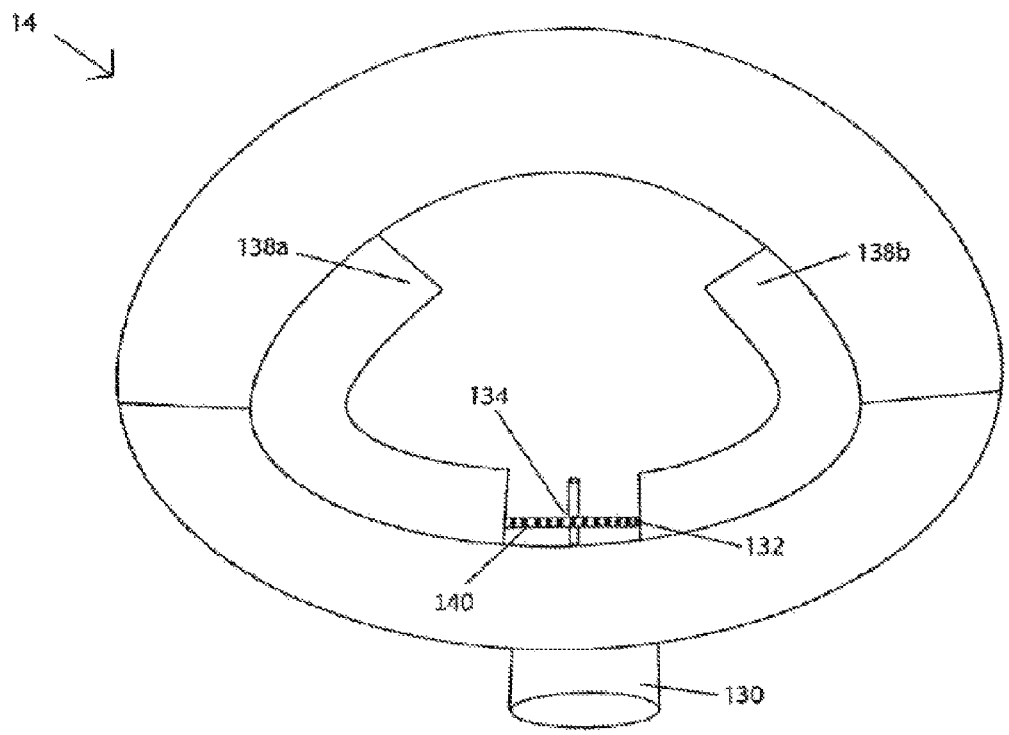
FIG. 14 shows a nasal dilator.

FIG. 14 is a perspective view of a nasal dilator 14, in accordance to some embodiments. In some embodiments, the mask pad 12 includes the nasal dilator 14. The nasal dilator 14 comprises two pads 138*a*, 138*b*, a pushing element 132, and an adjustment element 130. Each pad 138*a*, 138*b* is coupled to the pushing element 132. The pushing element 132 is coupled to the adjustment element 130 and is mechanically actuated by the adjustment element 130.

In some embodiments, the adjustment element 130 is a knob, or other similar device, and the pushing element 132 comprises of two threaded rods coupled to a gear 134. The two threaded rods 140 are coupled on one end to a pad 138*a* and on the other end to the gear 134. The gear 134 is attached to a support rod that is located approximately perpendicular to the threaded rods 140. The support rod connects to the mask pad 12 and is located approximately between the two pads 138*a*, 138*b*. The adjustment element 130 is turned by the user to adjust the desired level of nasal dilation by actuating the gear 134 and causing lateral movement of the pads 138*a*, 138*b* against the sides of the mask pad 12.

Although the disclosure has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the disclosure and should not be construed to limit the scope thereof.

What is claimed is:

1. A fluid preconditioning apparatus to pretreat fluids for an air disbursement machine, the fluid preconditioning apparatus comprising:
    a top portion, a base portion, and a partition disposed between the top portion and the base portion; and
    a hose sheath that connects to a tube outlet at the fluid preconditioning apparatus through an aperture disposed within the fluid preconditioning apparatus, wherein the hose sheath comprises:
        a flexible hose with a main lumen, an outer diameter, an exterior wall, and an interior wall; and
        at least one tube coupled to the flexible hose along at least one of the exterior wall and the interior wall of the flexible hose, the tube coupled on a first end to the fluid preconditioning apparatus and coupled on a second end to a mask pad, wherein the mask pad comprises:
        a pouch portion with an inlet port and an outlet port;
        a first fluid delivery tube coupled to the inlet port; and
        a second fluid delivery tube coupled to the outlet port;
            wherein the first fluid delivery tube transports heated fluid from the fluid preconditioning apparatus to the pouch portion and the second fluid delivery tube returns heated fluid back to the base portion for further pretreatment and continued disbursement;
    wherein the base portion comprises one or more exterior air vents, a gas inlet, a liquid inlet, a power supply, a gas treatment chamber, a gas flow generator, a liquid treatment chamber, and a liquid flow generator;
    wherein the gas treatment chamber pretreats gases for disbursement, and the liquid treatment chamber comprises a liquid filter that pretreats liquids for disbursement and pretreats liquids that have been returned back to the base portion after disbursement for continued disbursement.

2. The fluid preconditioning apparatus of claim 1, wherein the gas treatment chamber comprises a gas filter.

3. The fluid preconditioning apparatus of claim 1, wherein the liquid treatment chamber comprises a liquid heating element.

4. The fluid preconditioning apparatus of claim 1, wherein the gas to be disbursed is oxygen, air, carbon dioxide, or combinations thereof.

5. The fluid preconditioning apparatus of claim 4, wherein the gas is an aerosol.

6. The fluid preconditioning apparatus of claim 1, wherein the gas treatment chamber comprises:
    an ultraviolet (UV) ballast, a UV light source; and
    a controller for the gas flow generator.

7. The fluid preconditioning apparatus of claim 6, wherein the base portion comprises gas vents which direct treated gas to the air disbursement machine.

8. The fluid preconditioning apparatus of claim 1, wherein the liquid treatment chamber comprises:
    at least one water pump; and
    a UV light source, wherein the UV light source and the liquid filter are capable of disinfecting and removing particulates from the liquid, respectively.

9. The fluid preconditioning apparatus of claim 8, wherein the liquid treatment chamber comprises a liquid heating element.

10. The fluid preconditioning apparatus of claim 1, wherein the gas treatment chamber comprises a heating element.

11. The fluid preconditioning apparatus of claim 1, wherein the gas treatment chamber comprises a humidifier.

12. A fluid preconditioning apparatus to pretreat fluids for an air disbursement machine, the fluid preconditioning apparatus comprising:
- an enclosed top portion, a base portion coupled to the top portion, and a partition disposed between the top portion and the base portion; and
- a hose sheath that connects to a tube outlet at the fluid preconditioning apparatus through an aperture disposed within the fluid preconditioning apparatus;
- wherein the base portion comprises one or more exterior air vents, a gas inlet, a liquid inlet, a power supply, a gas treatment chamber, a gas flow generator, a liquid treatment chamber, and a liquid flow generator;
- wherein the base portion is coupled to the enclosed top portion via a means for moving the top portion horizontally across the base portion to provide an opening for a user to insert or remove the air disbursement machine into the enclosed top portion;
- wherein the gas treatment chamber pretreats gases for disbursement, and the liquid treatment chamber comprises a liquid filter that pretreats liquids for disbursement and pretreats liquids that have been returned back to the base portion after disbursement for continued disbursement.

13. The fluid preconditioning apparatus of claim 12, wherein the base portion is coupled to the enclosed top portion by a hinge.

14. The fluid preconditioning apparatus of claim 12, wherein the enclosed top portion comprises a plurality of smaller portions, at least one of the smaller portions being configured to decouple from the base portion and at least one of the remaining smaller portions being permanently fixed to the base portion.

15. The fluid preconditioning apparatus of claim 12, wherein the gas treatment chamber comprises a gas filter.

16. The fluid preconditioning apparatus of claim 12, wherein the liquid treatment chamber comprises a liquid heating element.

17. The fluid preconditioning apparatus of claim 12, wherein the gas treatment chamber comprises:
- an ultraviolet (UV) ballast, a UV light source; and
- a controller for the gas flow generator.

18. The fluid preconditioning apparatus of claim 12, wherein the liquid treatment chamber comprises:
- at least one water pump; and
- a UV light source, wherein the UV light source and the liquid filter are capable of disinfecting and removing particulates from the liquid, respectively.

19. A fluid preconditioning apparatus to pretreat fluids for an air disbursement machine, the fluid preconditioning apparatus comprising:
- an enclosed top portion, a base portion coupled to the top portion, and a partition disposed between the top portion and the base portion; and
- a hose sheath that connects to a tube outlet at the fluid preconditioning apparatus through an aperture disposed within the fluid preconditioning apparatus;
- wherein the base portion comprises one or more exterior air vents, a gas inlet, a liquid inlet, a power supply, a gas treatment chamber, a gas flow generator, a liquid treatment chamber, and a liquid flow generator;
- wherein the base portion is coupled to the enclosed top portion by a hinge;
- wherein the gas treatment chamber pretreats gases for disbursement, and the liquid treatment chamber comprises a liquid filter that pretreats liquids for disbursement and pretreats liquids that have been returned back to the base portion after disbursement for continued disbursement.

20. The fluid preconditioning apparatus of claim 19, wherein the enclosed top portion comprises a plurality of smaller portions, at least one of the smaller portions being configured to decouple from the base portion and at least one of the remaining smaller portions being permanently fixed to the base portion.

* * * * *